US009877843B2

(12) United States Patent
Vickers et al.

(10) Patent No.: US 9,877,843 B2
(45) Date of Patent: Jan. 30, 2018

(54) SPINAL IMPLANT SYSTEM AND METHOD

(71) Applicant: Warsaw Orthopedic, Inc., Warsaw, IN (US)

(72) Inventors: Scott M. Vickers, Hernando, MS (US); Jared J. Diegmueller, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 15/006,225

(22) Filed: Jan. 26, 2016

(65) Prior Publication Data
US 2017/0209283 A1  Jul. 27, 2017

(51) Int. Cl.
*A61F 2/44* (2006.01)
*A61F 2/30* (2006.01)

(52) U.S. Cl.
CPC ............ *A61F 2/4455* (2013.01); *A61F 2/442* (2013.01); *A61F 2002/30115* (2013.01); *A61F 2002/30471* (2013.01); *A61F 2002/4415* (2013.01)

(58) Field of Classification Search
CPC .................. A61F 2/4455; A61F 2/4611; A61F 2310/00023; A61F 2002/30579; A61F 2002/2835; A61F 2002/4627; A61F 2/4465; A61F 2/4425; A61F 2220/0025; A61F 2002/30604

USPC ........ 606/246–249, 90–94; 623/17.11–17.16
See application file for complete search history.

(56) References Cited

U.S. PATENT DOCUMENTS

| | | | |
|---|---|---|---|
| 4,083,369 A | 4/1978 | Sinnreich | |
| 6,387,130 B1 | 5/2002 | Stone et al. | |
| 8,025,697 B2 | 9/2011 | McClellan et al. | |
| 8,454,617 B2 | 6/2013 | Schaller et al. | |
| 8,795,365 B2 | 8/2014 | Arcenio et al. | |
| 9,138,327 B1 | 9/2015 | McClellan | |
| 2006/0089642 A1* | 4/2006 | Diaz | A61B 17/70 606/60 |
| 2006/0189999 A1 | 8/2006 | Zwirkoski | |
| 2006/0265077 A1* | 11/2006 | Zwirkoski | A61B 17/7094 623/17.16 |
| 2007/0055272 A1* | 3/2007 | Schaller | A61B 17/70 606/90 |
| 2008/0125865 A1 | 5/2008 | Abdelgany | |
| 2011/0046740 A1* | 2/2011 | Chen | A61F 2/4455 623/17.16 |
| 2013/0110239 A1* | 5/2013 | Siegal | A61B 17/7098 623/17.16 |
| 2014/0277481 A1 | 9/2014 | Lee et al. | |

\* cited by examiner

*Primary Examiner* — Eduardo C Robert
*Assistant Examiner* — Tara R Carter

(57) ABSTRACT

A spinal implant comprises a plurality of members. At least one element connects the members. An agent is disposed with at least one of the members. The members and the agent are disposable between a configuration for simultaneous delivery to a surgical site and an implant configuration. Systems, spinal constructs, surgical instruments and methods are disclosed.

15 Claims, 3 Drawing Sheets

SPINAL IMPLANT SYSTEM AND METHOD

TECHNICAL FIELD

The present disclosure generally relates to medical devices for the treatment of musculoskeletal disorders, and more particularly to a spinal implant system and a method for treating a spine.

BACKGROUND

Spinal pathologies and disorders such as degenerative disc disease, disc herniation, spondylolisthesis, stenosis, osteoporosis, tumor, scoliosis and other curvature abnormalities, kyphosis and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, correction, discectomy, microdiscectomy, corpectomy, decompression, laminectomy, laminotomy, foraminotomy, facetectomy and implantable prosthetics. As part of these surgical treatments, spinal constructs including implants, such as, for example, bone fasteners, spinal rods and interbody devices can be used to provide stability to a treated region. For example, during surgical treatment, surgical instruments can be used to deliver components of the spinal constructs to the surgical site for fixation with bone to immobilize a joint. This disclosure describes an improvement over these prior technologies.

SUMMARY

In one embodiment, a spinal implant comprises a plurality of members. At least one element connects the members. An agent is disposed with at least one of the members. The members and the agent are disposable between a configuration for simultaneous delivery to a surgical site and an implant configuration. In some embodiments, systems, spinal constructs, surgical instruments and methods are provided.

BRIEF DESCRIPTION OF THE DRAWINGS

The present disclosure will become more readily apparent from the specific description accompanied by the following drawings, in which.

DETAILED DESCRIPTION

Figure 1:
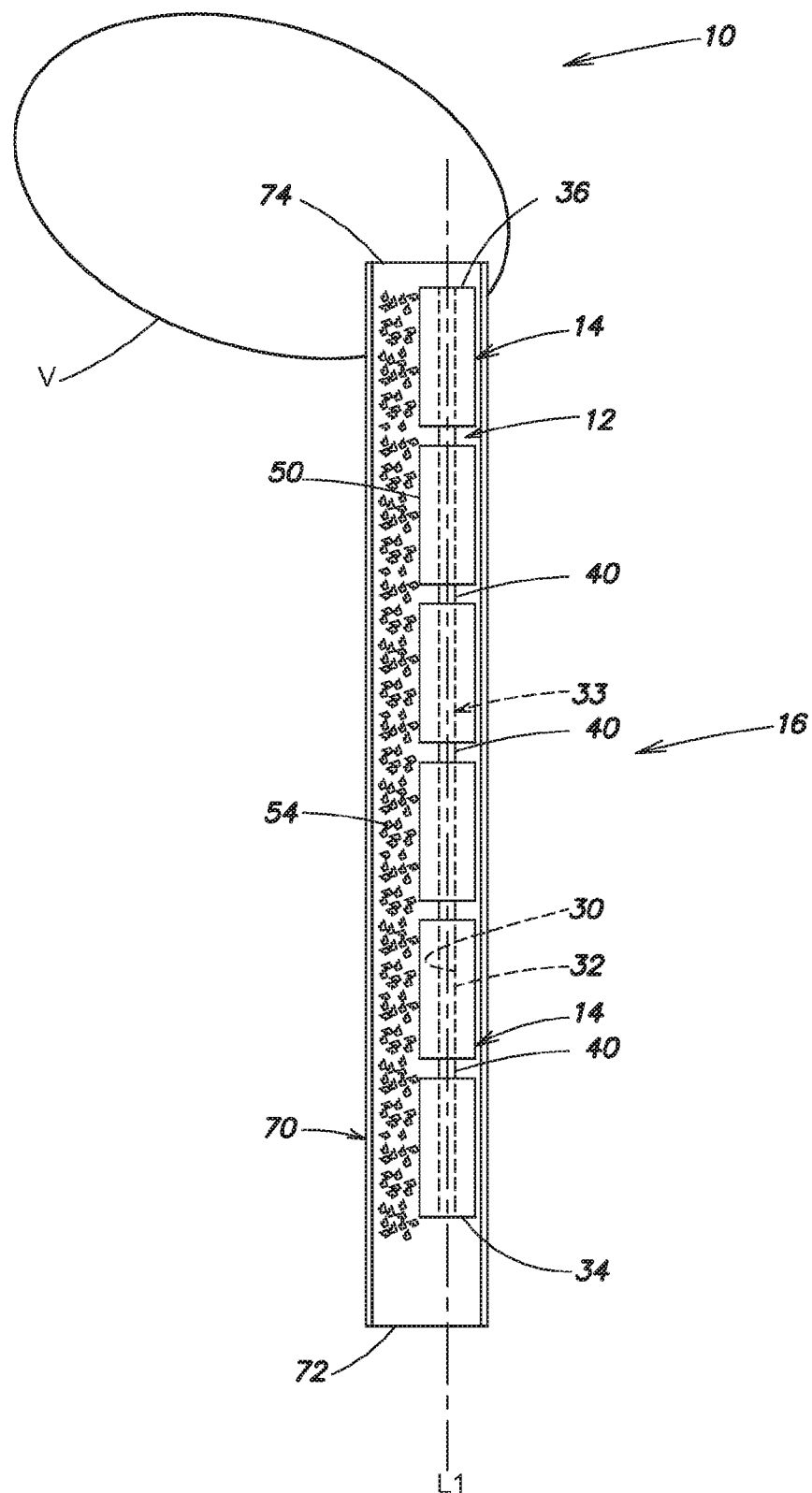
FIG. 1 is an axial view of components of one embodiment of a surgical system in accordance with the principles of the present disclosure disposed with vertebrae.

The exemplary embodiments of the surgical system and related methods of use disclosed are discussed in terms of medical devices for the treatment of musculoskeletal disorders and more particularly, in terms of a spinal implant system and a method for treating a spine.

In some embodiments, the spinal implant system includes an interbody implant including an agent, such as, for example, bone graft material. In some embodiments, the spinal implant system includes an interbody implant comprising a shape memory intervertebral body device with bone graft material. In some embodiments, the spinal implant system includes an interbody implant configured for minimally invasive delivery while maintaining an increased footprint when disposed with vertebrae.

In some embodiments, the spinal implant system includes an interbody implant configured for simultaneous delivery of bone graft material to a surgical site. In some embodiments, the interbody implant is configured to avoid the need for post-packing bone graft material after implant of the interbody implant. In some embodiments, this configuration provides for disposal of bone graft material with a center of the interbody implant while avoiding the need for post-packing bone graft material. In some embodiments, this configuration provides containment of bone graft material within the interbody implant. In some embodiments, this configuration provides containment of bone graft material within a center of the interbody implant that minimizes bone graft material migration. In some embodiments, the bone graft material is attached to the interbody implant. In some embodiments, the bone graft material is packed in a cannula employed to deliver the interbody implant to a surgical site. In some embodiments, the bone graft material includes adhesive. In some embodiments, the spinal implant system includes a mesh receptacle configured for disposal of bone graft material and the interbody implant.

In some embodiments, the interbody implant includes one or a plurality of members, such as, for example, load-bearing segments. In some embodiments, the load bearing segments include a material, such as, for example, polyetheretherketone (PEEK), stainless steel and/or titanium. In some embodiments, the load bearing segments are connected by one or more elements including a material, such as, for example, a metallic or polymeric shape-memory material.

In some embodiments, the interbody implant is disposable in an initial or first configuration. In some embodiments, the initial configuration facilitates minimally-invasive delivery of the interbody implant. In some embodiments, the initial configuration includes a linear configuration. In some embodiments, the interbody implant is moved from the first configuration into a second configuration.

In some embodiments, the interbody implant is actuated by application of a stimulus, such as, for example, a change in temperature to move between a first configuration and a second configuration. In some embodiments, the interbody implant is actuated by application of a stimulus, such as, for example, heat, cold and/or physical force to move the interbody implant between a first configuration and a second configuration. In some embodiments, the first configuration includes the interbody implant disposed in a straight configuration to facilitate introduction and delivery of the interbody implant into an intervertebral disc space.

In some embodiments, the interbody implant is actuated by application of a stimulus, as described herein, to the one or more elements connecting the segments to move the one or more elements between a first configuration and a second configuration. In some embodiments, the memory shape of the elements connecting the segments can comprise a straight shape for introduction and delivery of the interbody implant into an intervertebral disc space such that application of a stimulus, as described herein, causes the memory shape of the elements to return to a circular shape of the interbody implant. In some embodiments, the interbody implant is configured to alter its shape such that the load-bearing segments adopt the second configuration.

In some embodiments, the bone graft material is delivered alongside the interbody implant in the first configuration by attaching the bone graft material to the interbody implant. In some embodiments, the bone graft material is delivered adjacent to the interbody implant in the first configuration. In some embodiments, the bone graft material is enclosed within a cavity formed by the interbody implant in the second configuration. In some embodiments, the bone graft material is contained within a center portion of the interbody implant. In some embodiments, the first configuration facilitates delivery. In some embodiments, the second configuration facilitates load bearing and bone graft containment.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. The present disclosure may also be alternatively employed with procedures for treating the lumbar, cervical, thoracic, sacral and pelvic regions of a spinal column. The system and methods of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. As used in the specification and including the appended claims, the term "tissue" includes soft tissue, ligaments, tendons, cartilage and/or bone unless specifically referred to otherwise.

Figure 2:
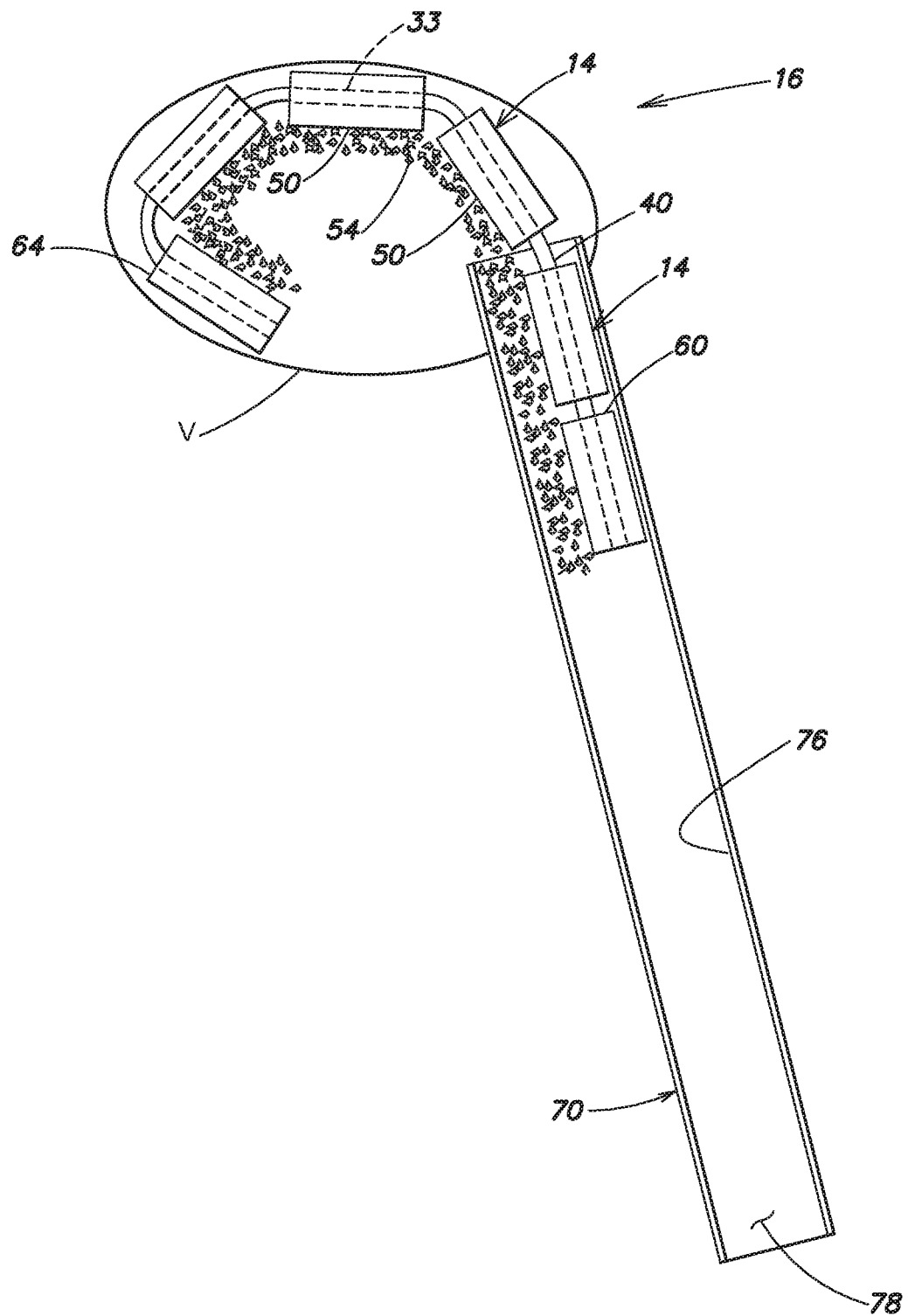
FIG. 2 is an axial view of components of one embodiment of a surgical system in accordance with the principles of the present disclosure disposed with vertebrae.
Figure 3:
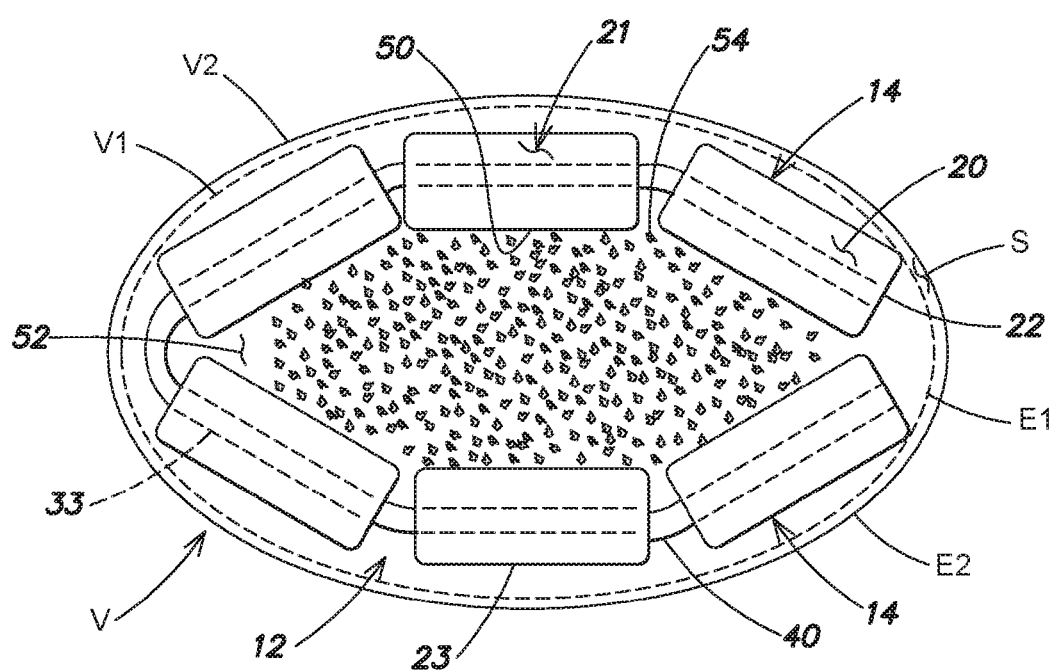
FIG. 3 is an axial view of components of one embodiment of a surgical system in accordance with the principles of the present disclosure disposed with vertebrae.

The following discussion includes a description of a surgical system and related methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-3, there are illustrated components of a surgical system such as, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including PEEK, polyetherketoneketone (PEKK) and polyetherketone (PEK), carbon-PEEK composites, PEEK-$BaSO_4$ polymeric rubbers, polyethylene terephthalate (PET), fabric silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate such as hydroxyapatite (HA), corraline HA, biphasic calcium phosphate, tricalcium phosphate, or fluorapatite, tri-calcium phosphate (TCP), HA-TCP, calcium sulfate, or other resorbable polymers such as polyaetide, polyglycolide, polytyrosine carbonate, polycaroplaetohe and their combinations, biocompatible ceramics, mineralized collagen, bioactive glasses, porous metals, bone particles, bone fibers, morselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-β), osteoblast cells, growth and differentiation factor (GDF), insulin-like growth factor 1, platelet-derived growth factor, fibroblast growth factor, or any combination thereof.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 is employed, for example, with a fully open surgical procedure, a minimally invasive procedure including percutaneous techniques, and mini-open surgical techniques to deliver and introduce instrumentation and/or an implant, such as, for example, an interbody implant, at a surgical site of a patient, which includes, for example, a spine having vertebrae V, as shown in FIGS. 1-3.

Spinal implant system 10 includes a spinal implant 12. Spinal implant 12 includes a plurality of members, such as, for example, a plurality of interconnected links 14 that define a link configuration 16. Links 14 are relatively movable such that link configuration 16 is disposable between a delivery and/or introduction configuration, as shown in FIG. 1, and an implant configuration, as shown in FIG. 3.

In some embodiments, in the delivery and/or introduction configuration, link configuration 16 includes a linear configuration, as shown in FIG. 1. In some embodiments, in the implant configuration, links 14 are articulated into a non-linear link configuration 16, for example an arcuate configuration, as shown in FIG. 3. In some embodiments, one or more of links 14 may have the same, different and/or alternate configurations, such as, for example, oval, round, cylindrical, oblong, triangular, rectangular, polygonal having planar or arcuate side portions, irregular, uniform, non-uniform, consistent, variable, horseshoe shape, U-shape or kidney bean shape. In some embodiments, all or only a portion, overall and/or in cross section, of link configuration 16 may be variously configured, such as, for example, elliptical, round, oblong, triangular, rectangular, polygonal having planar or arcuate side portions, irregular, uniform, non-uniform, consistent, variable, staggered, horseshoe shape, U-shape, barrel shape or kidney bean shape, and/or alternate dimension, such as, for example, the same, different, variable, tapered, uniform height, thickness, width and/or length.

Each link 14 includes a vertebral engaging surface 20 and a vertebral engaging surface 22. Surfaces 20 define a vertebral engaging surface 21 of link configuration 16 and are configured to engage endplate tissue of a vertebral body, such as, for example, an endplate E1 of a vertebral level V1, as shown in phantom in FIG. 3. Surfaces 22 define a vertebral engaging surface 23 of link configuration 16 and are configured to engage endplate tissue of a vertebral body, such as, for example, an endplate E2 of a vertebral level V2, as shown in FIG. 3. In some embodiments, surface 20 and/or surface 22 may be rough, textured, porous, semi-porous, dimpled, knurled, toothed, grooved and/or polished to facilitate engagement with tissue. In some embodiments, surface 20 and/or surface 22 may be substantially planar.

Link 14 includes an inner surface 30 that defines a longitudinal cavity, such as, for example, a channel 32. Each channel 32 extends through link configuration 16 to define a passageway 33 of spinal implant 12. Passageway 33 extends between an end 34 and an end 36 of link configuration 16. In the delivery and/or introduction configuration, as shown in FIG. 1, links 14 extend along an axis L1 defined by link configuration 16. Passageway 33 is configured for disposal of an element, such as, for example, a rod 40 configured to connect links 14, as described herein. In some embodiments, one or more channels 32 and/or passageway 33 may be co-axial, spaced apart, offset, angularly offset and/or in parallel alignment relative to link configuration 16.

In some embodiments, spinal implant 12 includes one or a plurality of elements configured to connect links 14. In some embodiments, spinal implant 12 includes a single, continuous element that connects links 14. In some embodiments, spinal implant 12 includes a plurality of elements, which include articulated segments to connect links 14. In some embodiments, spinal implant 12 includes a plurality of elements, which include separate and/or individual rods and/or segments that connect links 14. In some embodiments, spinal implant 12 includes a plurality of elements, which include multiple, discreet rods and/or segments that engage end surfaces of individual links 14 to connect adjacent links 14. In some embodiments, the individual links 14 include a solid configuration.

In some embodiments, as shown in FIGS. 1-3, rod 40 comprises a shape memory material and extends between an end 60 and an end 64 in a monolithic configuration. Shape memory rod 40 is disposed with passageway 33 and connects links 14 to move link configuration 16 between the delivery and/or introduction configuration and the implant configuration, as described herein. In some embodiments, in the delivery and/or introduction configuration, shape memory rod 40 disposes link configuration 16 in a deformed linear configuration, and in the implant configuration, shape memory rod 40 disposes link configuration 16 in an arcuate non-deformed configuration.

In some embodiments, shape memory rod 40 is configured for exposure to a temperature stimulus causing shape memory rod 40 to deform and move link configuration 16 between the delivery and/or introduction configuration, and the implant configuration. For example, shape memory rod 40 is initially disposed in an arcuate non-deformed configuration at a relatively low temperature and/or cold state, which is below a selected shape memory material transformation temperature (e.g., the transformation temperature from martensite to austenite). Shape memory rod 40 can be bent or stretched to a deformed linear configuration and will hold the linear configuration until heated above the transition temperature. In some embodiments, shape memory rod 40 may be exposed to a temperature stimulus for deformation to the delivery and/or introduction configuration. Shape memory rod 40 is heated to the transition temperature or above and shape memory rod 40 changes shape to the arcuate orientation in the implant configuration. In some embodiments, shape memory rod 40 can be heated via a mechanical device and/or with body temperature of a patient.

In some embodiments, shape memory rod 40 is configured for exposure to a force stimulus, for example, via work hardening and/or as described herein, to move link configuration 16 between the delivery and/or introduction configuration, and the implant configuration. In some embodiments, shape memory rod 40 is configured for exposure to an electrical, magnetic, light or chemical stimulus to move link configuration 16 between the delivery and/or introduction configuration, and the implant configuration. In some embodiments, shape memory rod 40 is fabricated from a shape memory polymer, cobalt-chrome alloys, copper-aluminum-nickel alloys, nickel-titanium alloys and/or superelastic metallic alloys (e.g., Nitinol, super elasto-plastic metals, such as GUM METAL®, super-elastic titanium alloys), one way memory effect alloys and/or two way memory effect alloys. In some embodiments, shape memory rod 40 includes a wire, tether and/or band.

In some embodiments, rod 40 includes a plurality of segments configured to articulate link configuration 16 between the delivery and/or introduction configuration, and the implant configuration. In some embodiments, rod 40 may be rigid or semi-rigid and may be constructed from metals, including for example stainless steel, cobalt-chrome, titanium, and shape memory alloys, as described herein. In some embodiments, rod 40 may be straight, curved, or comprise one or more curved portions along its length. In some embodiments, all or only a portion of rod 40 have a flexible or elastic configuration and/or have elastic and/or flexible properties, similar to the properties from materials, such as, for example, fabric, silicone, polyurethane, silicone-polyurethane, copolymers, rubbers, polyolefin rubber, elastomers, thermoplastic elastomers, thermoset elastomers and elastomeric composites.

Each link 14 includes a surface 50. Each surface 50 is configured for disposal and/or attachment with an agent, such as, for example, bone graft 54, as described herein. Surfaces 50 define an inner cavity 52 of spinal implant 12 with link configuration 16 disposed in the implant configuration, as shown in FIG. 3. Cavity 52 is configured for disposal of at least bone graft 54, as described herein. Cavity 52 is formed as link configuration 16 is moved into the implant configuration. In some embodiments, cavity 52 includes an elliptical configuration. In some embodiments, cavity 52 may include various configurations, such as, for example, round, cylindrical, oblong, triangular, rectangular, polygonal having planar or arcuate side portions, irregular, uniform, non-uniform, consistent, variable, staggered, horseshoe shape, U-shape, barrel shape or kidney bean shape, and/or alternate dimension, such as, for example, the same, different, variable, tapered, uniform height, thickness, width and/or length. In some embodiments, one or more surfaces 50 may be rough, textured, porous, semi-porous, dimpled, knurled, toothed, grooved and/or polished.

In the implant configuration, surfaces 50 are configured to surround and contain bone graft 54 such that bone graft 54 is disposed in a center portion of spinal implant 12, as shown in FIG. 3. In some embodiments, bone graft 54 is disposed offset relative to a center portion of spinal implant 12. In some embodiments, bone graft 54 is disposed along an outer surface of links 14 in the implant configuration.

In some embodiments, bone graft 54 is selectively disposed along surfaces 50 with all or only a portion of link configuration 16 such that bone graft 54 is configured for simultaneous delivery with spinal implant 12 to a surgical site, as described herein. In some embodiments, bone graft 54 is simultaneous delivered with link configuration 16 to a surgical site within a surgical instrument, such as, for example, a cannula 70, as described herein. In some embodiments, bone graft 54 is packed with spinal implant 12 during delivery. In some embodiments, bone graft 54 is adhered to links 14. In some embodiments, bone graft 54 may include, such as, for example, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, TCP, HA-TCP, calcium sulfate, or other resorbable polymers such as polyaetide, polyglycolide, polytyrosine carbonate, polycaroplaetohe and their combinations.

In some embodiments, bone graft 54 may include a mesh bag containing bone graft material. In some embodiments, spinal implant 12 includes a mesh bag containing link configuration 16 and bone graft 54. In some embodiments, a suitable mesh bag includes MAGNIFUSE® Bone Graft, available from Medtronic, which comprises surface demineralized bone chips mixed with non-demineralized cortical bone fibers or fully demineralized bone fibers sealed in an absorbable PGA mesh bag or pouch.

In assembly, operation and use, as shown in FIGS. 1-3, spinal implant system 10, similar to the systems and methods described herein, is employed with a surgical procedure for treatment of a spinal disorder, such as those described herein, affecting a section of a spine of a patient. For example, spinal implant system 10 may be employed with surgical procedures, such as, for example, discectomy, laminectomy, fusion, laminotomy, laminescenty, nerve root retraction, foramenotomy, facetectomy, decompression, spinal nucleus or disc replacement.

In some embodiments, spinal implant system 10 is employed with a lumbar interbody fusion including surgical arthrodesis to immobilize a joint for treatment of an applicable condition or injury of an affected section of a spinal column and adjacent areas within a body. For example, vertebrae V include a vertebra V1 and a vertebra V2. In some embodiments, vertebrae V1, V2 include diseased and/or damaged vertebra and intervertebral discs. In some embodiments, components of spinal implant system 10 are configured for insertion with a vertebral space between vertebrae V1, V2 and spinal implant 12 includes load bearing surfaces, such as, for example, links 14, as described herein, to space apart articular joint surfaces, provide support and maximize stabilization of vertebrae V.

In use, to treat the affected section of vertebrae V, a medical practitioner obtains access to a surgical site including vertebrae V in any appropriate manner, such as through incision and retraction of tissues. In some embodiments, spinal implant system 10 may be used in any existing surgical method or technique including open surgery, mini-open surgery, minimally invasive surgery and percutaneous surgical implantation, whereby vertebrae V is accessed through a mini-incision, or sleeve, such as, for example, cannula 70, which provides a protected passageway and/or surgical pathway to the area. Once access to the surgical site is obtained, a surgical procedure, as described herein, is performed for treating the spine disorder. The diseased and/or damaged portion of vertebrae V, which may include diseased and/or damaged intervertebral discs, are removed to create a vertebral space between vertebrae V1, V2.

In some embodiments, a minimally invasive surgical procedure is employed and a surgeon makes one or more incisions in the skin of a patient's back over vertebrae V to be treated. Spinal implant system 10 includes cannula 70, which extends between ends 72, 74. Cannula 70 includes a surface 76 that defines a channel 78. Cannula 70 is passed through the incision and end 74 is disposed adjacent the surgical site and the vertebral space between vertebrae V1, V2.

A preparation instrument (not shown) is employed to remove disc tissue, fluids, adjacent tissues and/or bone, and scrape and/or remove tissue from endplate surfaces E1 of vertebra V1 and/or endplate surface E2 of vertebra V2. In some embodiments, an annulotomy and/or discectomy is performed with a surgical instrument (not shown) with x-ray confirmation of the starting point that is central on one or more intervertebral spaces.

In some embodiments, a probe is passed into the vertebral space between vertebrae V1, V2 to secure its location. Fluoroscopy, image guidance and/or surgical navigation, as described herein, are used to confirm proper probe alignment into the vertebral space. In some embodiments, a guide wire is placed through cannula 70 into the vertebral space and positioning is confirmed with fluoroscopy. Instruments, such as, for example, a Cobb, mallet, shaver, serrated curettes, rasp, a ring curette, a uterine curette and/or combo tools are utilized to perform a discectomy of the vertebral space. The vertebral space is distracted until adequate disc space height is obtained.

In some embodiments, shape memory rod 40 is initially disposed in an arcuate non-deformed configuration, as described herein. Shape memory rod 40 is configured such that link configuration 16 is deformable to a linear configuration in the delivery and/or introduction configuration, as shown in FIG. 1. An agent including bone graft 54 is packed and/or positioned along surfaces 50 for simultaneous delivery with links 14 to the surgical site and the vertebral space between vertebrae V1, V2.

In the delivery and/or introduction configuration, link configuration 16 and the agent including bone graft 54 are disposed within channel 78. Link configuration 16 and the agent including bone graft 54 are simultaneously delivered to the surgical site and introduced to the vertebral space between vertebrae V1, V2, as shown in FIG. 2. Shape memory rod 40 is exposed to a temperature stimulus, for example, heated, as described herein, to the transition temperature or above and shape memory rod 40 changes shape to the arcuate orientation in the implant configuration, as shown in FIG. 3. In the implant configuration, surfaces 50 form cavity 52 and surround and contain the agent including bone graft 54 therein adjacent the vertebral space between vertebrae V1, V2.

Links 14 comprise load bearing segments such that spinal implant 12 provides a footprint that improves stability and decreases the risk of subsidence into tissue of vertebrae V1, V2. In some embodiments, links 14 comprise load bearing segments such that spinal implant 12 provides height restoration between vertebrae V1, V2, decompression, restoration of sagittal and/or coronal balance and/or resistance of subsidence into vertebral endplates of vertebrae V1, V2. In some embodiments, spinal implant 12 engages and spaces apart opposing endplate surfaces of vertebrae V1, V2 and is secured within the vertebral space to stabilize and immobilize portions of vertebrae V in connection with bone growth for fusion and fixation of vertebrae V1, V2.

Upon completion of a procedure, as described herein, the surgical instruments, assemblies and non-implanted components of spinal implant system 10 are removed and the incision(s) are closed. One or more of the components of spinal implant system 10 can be made of radiolucent materials such as polymers. Radiopaque markers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal implant system 10. In some embodiments, spinal implant system 10 may include one or a plurality of plates, spinal rods, connectors and/or bone fasteners for use with a single vertebral level or a plurality of vertebral levels.

In some embodiments, spinal implant system 10 includes an agent, which may be disposed, packed, coated or layered within, on or about the components and/or surfaces of spinal implant system 10. In some embodiments, the agent may include bone growth promoting material, as described herein, to enhance fixation of the components and/or surfaces of spinal implant system 10 with vertebrae. In some embodiments, the agent may include one or a plurality of therapeutic agents and/or pharmacological agents for release, including sustained release, to treat, for example, pain, inflammation and degeneration.

In some embodiments, spinal implant system 10 may comprise the use of microsurgical and image guided technologies, such as, for example, surgical navigation components employing emitters and sensors, which may be employed to track introduction and/or delivery of the components of spinal implant system 10 including the surgical instruments to a surgical site. See, for example, the surgical navigation components and their use as described in U.S. Pat. Nos. 6,021,343, 6,725,080, 6,796,988, the entire contents of each of these references being incorporated by reference herein.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal implant comprising: a plurality of members; at least one element connecting the members, the at least one element including a surface; and an agent adjacent to and contacting an exterior surface of the members, the members and the agent being disposable between a linear configuration and an implant configuration for simultaneous delivery to a surgical site, when in the linear configuration, the agent being disposed along a longitudinal axis of the exterior surface of the members and contacting the exterior surface of the members, and when in the implant configuration, the implant is in an elliptical configuration that defines an inner cavity, the agent being disposed within the inner cavity; and the surface is configured to surround and contain the agent such that the agent is disposed in a center portion of the spinal implant, wherein the agent comprises a bone graft material and is disposed on and contacts the exterior surface of the members in the elliptical configuration.

2. A spinal implant as recited in claim 1, wherein the members comprise a plurality of interconnected links.

3. A spinal implant as recited in claim 1, wherein the members define a surface that engages a first vertebral surface and a surface that engages a second vertebral surface.

4. A spinal implant as recited in claim 1, wherein each of the members define a passageway for disposal of the at least one element.

5. A spinal implant as recited in claim 1, wherein the at least one element includes a plurality of separate elements.

6. A spinal implant as recited in claim 1, wherein the at least one element includes a shape memory material.

7. A spinal implant as recited in claim 1, wherein the at least one element is monolithic.

8. A spinal implant as recited in claim 1, wherein the at least one element includes a plurality of articulated segments.

9. A spinal implant as recited in claim 1, wherein the at least one element is exposed to a temperature stimulus to move the members between the configurations.

10. A spinal implant as recited in claim 1, wherein the at least one element is exposed to a force stimulus to move the members between the configurations.

11. A spinal implant as recited in claim 1, wherein the implant configuration further includes an arcuate configuration.

12. A spinal implant as recited in claim 1, wherein the implant consists of only a plurality of members, at least one element connecting the members and the agent.

13. A spinal implant comprising: a plurality of members engageable with a first vertebral surface and a second vertebral surface; a shape memory element that connects the members, the shape memory element having an outer surface; and an agent adjacent to and contacting an exterior surface of the members, the members and the agent being disposable between a linear configuration and an implant configuration for simultaneous delivery to a surgical site, when in the linear configuration, the agent being disposed along a longitudinal axis of the exterior surface of the members and contacting the exterior surface of the members, and the element being reactive to a stimulus to dispose the members in an implant configuration, wherein in the implant configuration, the outer surface forms a cavity and contains the agent surrounding therein, the implant when implanted being adjacent to a vertebral space between the first vertebral surface and the second vertebral surface, wherein the agent comprises a bone graft material and is disposed on and contacts the exterior surface of the members in the elliptical configuration.

14. A spinal implant system comprising: a spinal implant including a plurality of members connected by at least one element, the at least one element having an outer surface, and an agent adjacent to and contacting an exterior surface of the members; and a cannula, the members and the agent being disposable between a linear configuration and an implant configuration for simultaneous delivery within the cannula, when in the linear configuration, the agent being disposed along a longitudinal axis of the exterior surface of the members and contacting the members, and when in the implant configuration, the outer surface forms a cavity and contains the agent surrounding therein, wherein the agent comprises a bone graft material and is disposed on and contacts the exterior surface of the members in the liner configuration and elliptical configuration.

15. A spinal implant system as recited in claim 14, wherein the implant configuration includes an arcuate configuration.

* * * * *